US00PP08474P

United States Patent [19]

VandenBerg

[11] Patent Number: Plant 8,474

[45] Date of Patent: Nov. 23, 1993

[54] CHRYSANTHEMUM PLANT NAMED QUINCY

[75] Inventor: Cornelis P. VandenBerg, Salinas, Calif.

[73] Assignee: Yoder Brothers, Inc., Barberton, Ohio

[21] Appl. No.: 935,268

[22] Filed: Aug. 27, 1992

[51] Int. Cl.[5] ..... A01H 5/00

[52] U.S. Cl. ..... Plt./82.2

[58] Field of Search ..... Plt./74.1, 82.2

*Primary Examiner*—Howard J. Locker

*Attorney, Agent, or Firm*—Foley & Lardner

[57] ABSTRACT

A Chrysanthemum plant named Quincy particularly characterized by its flat capitulum form; daisy capitulum type; yellow ray floret color; diameter across face of capitulum of 114 to 124 mm when fully opened, when grown as a pinched disbudded pot mum; photoperiodic flowering response to short days of 51 to 59 days; plant height with 0 to 1 application of 2500 ppm B-9 SP, ranges from 23 to 28 cm when grown as a pinched pot mum with 4 cuttings in a 15 cm pot; branching pattern is semi-spreading, each plant having 3 to 4 laterals after pinch; and recommended as disbud pot mum.

3 Drawing Sheets

The present invention comprises a new and distinct cultivar of Chrysanthemum, botanically known as *Dendranthema grandiflora*, referred to by the cultivar name Quincy.

Quincy, identified as 5141 (88-121006), was originated from a cross made by Cornelis P. VandenBerg in a controlled breeding program in Salinas, Calif., in 1986.

The female parent of Quincy was an unnamed seedling identified as 5211 (82-404009), and described as a yellow disbud daisy pot mum with a flowering response of 53 to 59 days under normal conditions in Salinas, Calif.; plant height of 23 to 28 cm with 15 to 16 long days after sticking unrooted cuttings prior to start of short days and with one to two applications of 2500 ppm B-9 SP when grown as a pinched pot mum; branching habit of 3 to 5 laterals developing after pinch; and diameter of capitulum of 133 to 149 mm. The female parent was discarded from all programs on May 28, 1992.

The male parent of Quincy was an unnamed seedling, identified as 5502 (83-436012) and described as a white flat disbud daisy pot mum with a flowering response to short days of 50 to 59 days under normal conditions in Salinas, Calif.; plant height of 28 to 33 cm with 15 to 16 long days after sticking unrooted cuttings prior to start of short days and 1 to 3 applications of 2500 ppm B-9 SP when grown as a pinched pot mum; branching habit of 3 to 5 laterals developing after pinch; and diameter of capitulum of 114 to 127 mm.

Quincy was discovered and selected as one flowering plant within the progeny of the stated cross by Cornelis P. VandenBerg in October 1988, in a controlled environment in Salinas, Calif.

The first act of asexual reproduction of Quincy was accomplished when vegetative cuttings were taken from the initial selection in December 1988 in a controlled environment in Salinas, Calif., by technicians working under supervision of Cornelis P. VandenBerg.

Horticultural examination of controlled flowerings of successive plantings has shown that the unique combination of characteristics as herein disclosed for Quincy are firmly fixed and are retained through successive generations of asexual reproduction.

Quincy has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Quincy, which, in combination, distinguish this Chrysanthemum as a new and distinct cultivar:

1. Flat capitulum form.
2. Daisy capitulum type.
3. Yellow ray floret color.
4. Diameter across face of capitulum of 114 to 124 mm when fully opened, when grown as a pinched disbudded pot mum.
5. Photoperiodic flowering response to short days of 51 to 59 days.
6. Plant height with 15 to 16 long days after sticking unrooted cuttings, and with 0 to 1 application of 2500 ppm B-9 SP, ranging from 23 to 28 cm when grown as a pinched pot mum with 4 cuttings in a 15 cm pot.
7. Branching pattern is semi-spreading, each plant having 3 to 4 laterals after pinch.
8. Recommended as disbud pot mum.

The accompanying photographic drawings show typical inflorescence and leaf characteristics of Quincy, with the colors being as nearly true as possible with illustrations of this type.

Sheet 1 is a top perspective color photograph of Quincy grown as a pinched disbudded pot mum with 4 cuttings in a 15 cm pot.

Sheet 2 is a black and white photograph of three views of the inflorescence of Quincy.

Sheet 3 is a black and white photograph showing the upper and under sides of the leaves of Quincy at 3 stages of development (mature, intermediate and immature). In sheets 2 and 3 a measuring tape in centimeters has been added.

Of the commercial cultivars known to the inventor, the most similar in comparison to Quincy is the cultivar Miramar, disclosed in U.S. Plant Pat. No. 7,469. Reference is made to attached Chart A, which compares certain characteristics of Quincy to the same characteristics of Miramar.

Similar traits are capitulum form, diameter of capitulum, flowering response to short days, plant height, semi-spreading branching pattern and recommendation as a disbudded pot mum. The ray floret color of both Quincy and Miramar is described as yellow. However, ray floret color of Quincy is significantly lighter than the intense deep yellow ray floret color of Miramar. Quincy has a daisy capitulum type, while Miramar has a spooned daisy capitulum type. In comparison to Miramar, Quincy has an average of one lateral per plant less developing after pinch than Miramar.

In the following description color references are made to The Royal Horticultural Society Colour Chart. The color values were determined on plant material grown as a pinched disbudded pot mum in Salinas, Calif. on Mar. 25, 1992.

Classification:

*Botanical.*—*Dendranthema grandiflora* cv Quincy.

*Commercial.*—Daisy disbud mum.

INFLORESCENCE

A. Capitulum:

*Form.*—Flat.

*Type.*—Daisy.

*Diameter across face.*—114 to 124 mm when fully opened.

B. Corolla of ray florets:

*Color (general tonality from a distance of three meters).*—Yellow.

*Color (upper surface).*—3A.

*Color (under surface).*—5C.

*Shape of petals.*—Straight, pointed, slightly ribbed.

C. Corolla of disc florets:

*Color (mature).*—14B.

*Color (immature).*—144A to 144B.

D. Reproductive organs:

*Androecium.*—Present on disc florets only; scant pollen.

*Gynoecium.*—Present on both ray and disc florets.

PLANT

A. General appearance:

*Height.*—23 to 28 cm when grown as a pinched pot mum in a 15 cm pot with 15 to 16 long days after sticking unrooted cuttings and 0 to 1 applications of 2500 ppm B-9 SP.

*Branching pattern.*—Semi-spreading, with 3 to 4 laterals after pinch.

B. Foliage:

*Color (upper surface).*—147A.

*Color (under surface).*—147B.

*Shape.*—See photograph.

CHART A

COMPARISON OF QUINCY AND MIRAMAR

| CULTIVAR | QUINCY | MIRAMAR |
|---|---|---|
| Ray floret color | Yellow | Yellow |
| Capitulum form and type | Flat<br>Daisy | Flat<br>Spooned daisy |
| Diameter across face of capitulum | 114 to 124 mm | 114 to 127 mm |
| Flowering response | 51 to 59 days | 53 to 58 days |
| Plant height with 15 to 16 long days | 23 to 28 cm | 23 to 28 cm |
| Branching pattern | Semi-spreading<br>3 to 4 laterals | Semi-spreading<br>4 to 5 laterals |
| Recommended as | Disbud pot mum | Disbud pot mum |

COMPARISONS MADE OF PLANTS GROWN AS PINCHED DISBUDDED POT MUMS IN SALINAS, CALIFORNIA

I claim:

1. A new and distinct Chrysanthemum plant named Quincy, as described and illustrated.

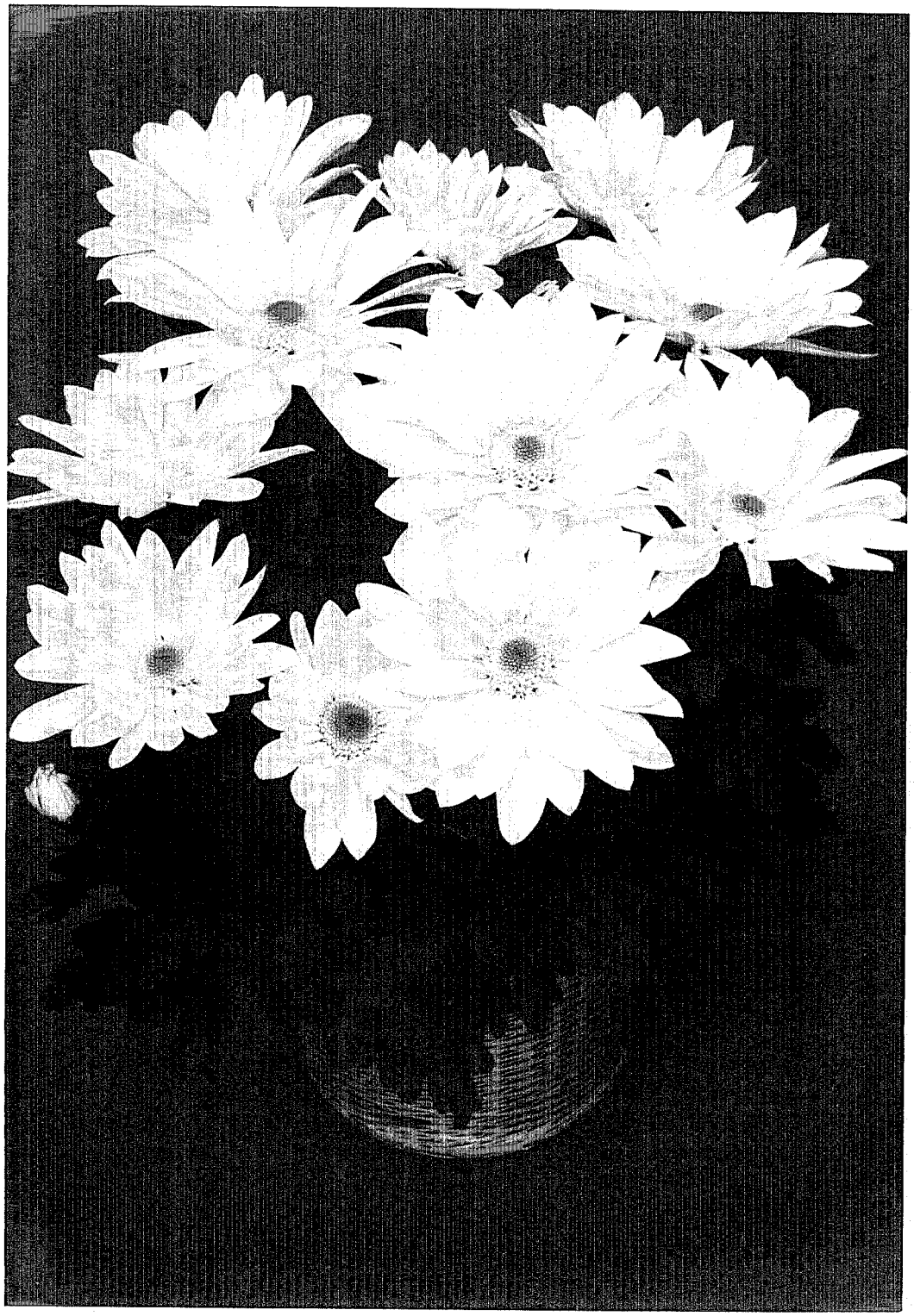

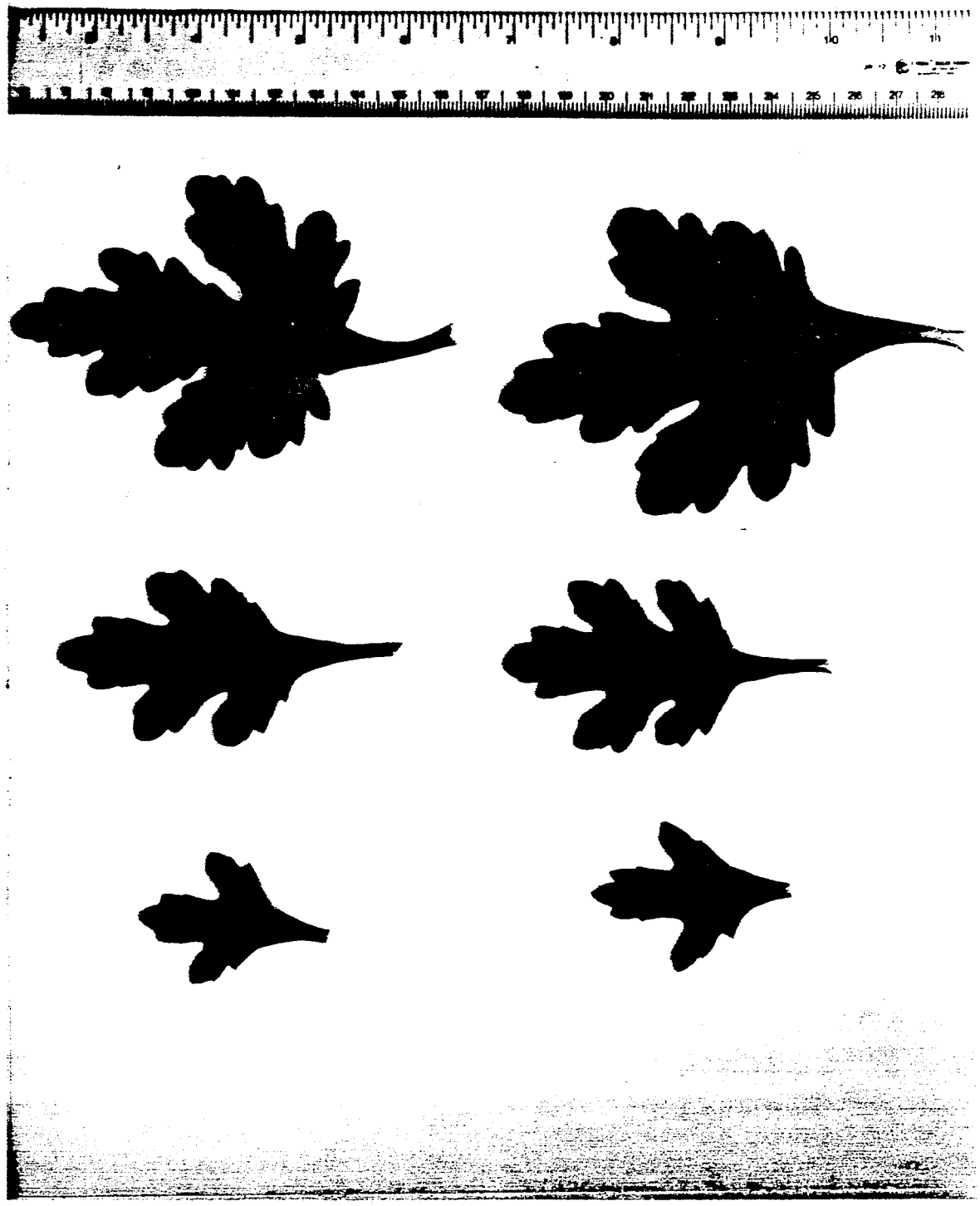

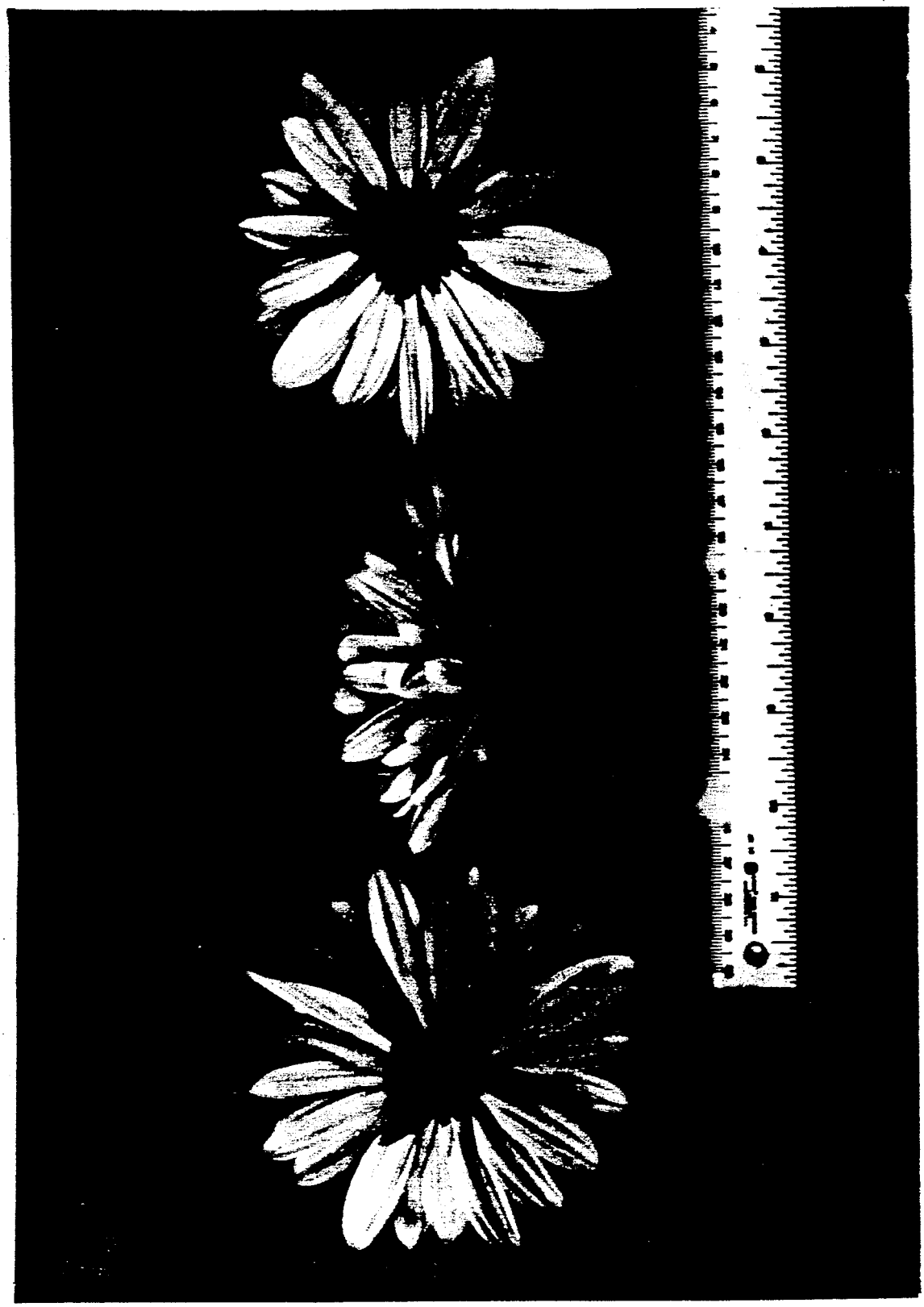

* * * * *